United States Patent [19]

Schwarz et al.

[11] Patent Number: 5,235,065

[45] Date of Patent: Aug. 10, 1993

[54] PROCESS FOR THE PREPARATION OF A D-(+)-BIOTIN INTERMEDIATE

[75] Inventors: Michael Schwarz, Gerau; Michael Casutt, Heppenheim; Jürgen Eckstein, Rossdorf, all of Fed. Rep. of Germany

[73] Assignee: Merck Patent Gesellschaft Mit Beschrankter Haftung, Darmstadt, Fed. Rep. of Germany

[21] Appl. No.: 846,105

[22] Filed: Mar. 5, 1992

[30] Foreign Application Priority Data

Mar. 6, 1991 [DE] Fed. Rep. of Germany ....... 4107121

[51] Int. Cl.$^5$ ............... C07D 495/04; C07D 491/04; C07D 333/32; C07D 473/00
[52] U.S. Cl. .......................... 548/303.7; 548/303.1
[58] Field of Search ................ 548/303, 303.7

[56] References Cited

U.S. PATENT DOCUMENTS

| | | | |
|---|---|---|---|
| 3,740,350 | 6/1973 | Shanefield | 252/512 |
| 3,740,416 | 6/1973 | Gerecke et al. | 548/303 |
| 3,876,656 | 4/1975 | Aoki et al. | 548/303 |
| 4,636,566 | 1/1987 | Holick et al. | 548/303 |
| 4,876,350 | 10/1989 | McGarrity et al. | 548/110 |
| 4,877,882 | 10/1989 | Poetsch et al. | 548/303 |

FOREIGN PATENT DOCUMENTS 0084377 7/1983 European Pat. Off. ......... 548/303.7

OTHER PUBLICATIONS

Rawal et al., J. Org. Chem. vol. 55, pp. 5181 to 5183 (1990).
Isaka et al., Jap. Bull. Pharm. Chem, vol. 88(8), pp. 1068-1073 (1968).
Oyke, "The Chemistry of Vitamins", Chapter 9, pp. 161-181 (1965).

*Primary Examiner*—Floyd D. Higel
*Attorney, Agent, or Firm*—Millen, White, Zelano & Branigan

[57] ABSTRACT

The present invention relates to a process for the preparation of heterocyclic compounds which are suitable as intermediates for the preparation of D-(+)-biotin, and to a process for the preparation of D-(+)-biotin itself. The invention further relates to intermediates in this process.

8 Claims, No Drawings

PROCESS FOR THE PREPARATION OF A D-(+)-BIOTIN INTERMEDIATE

BACKGROUND OF THE INVENTION

The present invention relates to a novel process for the preparation of heterocyclic compounds which are suitable as intermediates for the preparation of D-(+)-biotin, and to a process for the preparation of D-(+)-biotin itself. The invention further relates to novel intermediates in this process.

D-(+)-biotin is a substance which has been known for a long time, and there are therefore already a number of processes known for its preparation. Common to the processes of industrial interest is the necessity of adding the carboxybutyl side chain to the ring system at some stage. Various solutions are known for this, such as, for example, the synthesis of the side chain according to the scheme of linkage $C_4+C_1 \rightarrow C_5$ or alternative $(C_3+C_3-C_1=C_2) \rightarrow C_5$ (for example, Swiss Patent 556,867).

It is also known to link the side chain with the ring system in one step by means of a Wittig reaction (for example EP-A-0 084 377). However, all these processes have the disadvantage that they either proceed via a comparatively large number of reaction steps or else require a relatively large outlay to isolate the desired final product.

The introduction of the side chain by reaction of the thiolactone of the formula I with 4-(2,4,10-trioxaadamantyl)butylmagnesium bromide is additionally known from EP-A-0 154 225.

However, this process has various disadvantages which make it appear unsuitable in the case of industrial implementation.

The cis-1,3,5-cyclohexanetriol needed for the preparation of the Grignard reagent is only poorly accessible and must be recovered again by technically complicated isolation techniques after reaction has taken place. Moreover, the yields in this process are not adequate for industrial utilization.

SUMMARY OF THE INVENTION

There is therefore a need for a technically simple process according to which the side chain can be added to the ring system in good yield and in one reaction step if possible. This is now possible by means of the process according to the invention.

Upon further study of the specification and appended claims, further objects and advantages of this invention will become apparent to those skilled in the art.

This process is characterized in that the thiolactone of the formula I

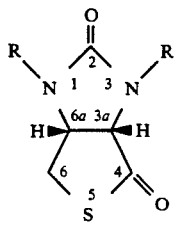

in which R is a benzyl group which is unsubstituted or substituted by one or two alkyl groups having 1-5 C atoms, is reacted with an organometallic compound of the formula II

in which Met is Li, MgCl or MgBr, preferably MgCl or MgBr, in particular MgCl, and $R^1$ is alkyl having 1 to 3 C atoms,
in that the compound thus obtained of the formula III

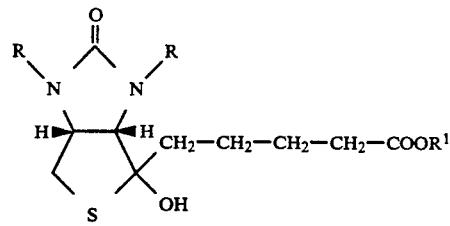

in which R and $R^1$ have the above meaning, is dehydrated, in that, in the compound thus obtained of the formula IV

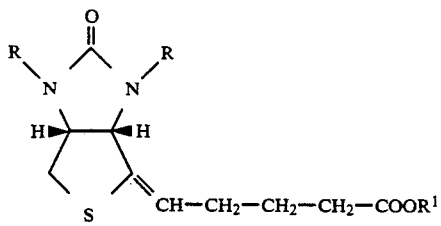

in which R and $R^1$ have the above meaning, the carboxyl group in the side chain is liberated by alkaline hydrolysis, and in that the compound thus obtained of the formula V

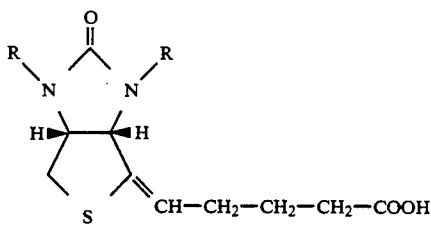

in which R has the above meaning or the side chain is liberated by hydrolysis with hydrogen bromide, and in that the compound thus obtained of formula V, in which R is H, is converted into D-(+)-biotin in a manner known per se.

The compounds of the formula I used as starting materials, and the compounds of the formulae IV and V prepared according to the invention are known compounds (for example EP 0 084 377 R=benzyl or EP 0 273 270 R=1-phenylethyl). The compounds of the formulae II and III, however, are novel and likewise a subject of the present invention.

The preparation of the compounds of the formula II can be carried out in analogy to known processes according to the following equation:

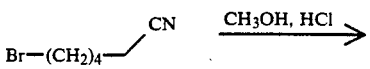

$$\overset{+NH_2Cl^{\ominus}}{\underset{\parallel}{Br-(CH_2)_4-C-OCH_3}} \xrightarrow[\text{hexane}]{R^1OH} Br-(CH_2)_4-C(OR^1)_3$$

(for example G. Caby et al., Org. Synthe. 67, 93-201 (1988)).

In the compounds of the formulae I to V, R is preferably an unsubstituted benzyl group or an (R or S)-(1-phenylethyl) group and $R^1$ is methyl, ethyl or propyl, in particular methyl.

$$Br-(CH_2)_4-C(OR^1)_3$$

tert. Butyllithium (e.g., B. C. Bohrer et. al., Syn. Lett. 601-2 (1990)) / Mg (e.g., V. H. Rawal, J. Org. Chem. 55 5181-83 (1990))

$$Li-(CH_2)_4-C(OR^1)_3 \qquad BrMg-(CH_2)_4-C(OR^1)_3$$

The reaction of the thiolactone of the formula I with an organometallic compound of the formula II can be carried out in a manner known per se, i.e., under the customary conditions for such a reaction. Expediently, this reaction is carried out in an organic solvent which is inert under the reaction conditions, for example in lower alkyl ether such as diethyl ether or a cyclic ether such as tetrahydrofuran, dioxane and the like and at a temperature of about $-78°$ C. to the boiling point of the solvent used, preferably at about $0°$ C. to about $50°$ C., in particular at room temperature. The reaction is completed in 0.5 to 5 hours depending on the temperature. As a rule 0.9 to 1.8 moles, preferably 1.0 to 1.3 moles, of organometallic-compound of the formula II are reacted with 1.0 mole of thiolactone of the formula I.

The orthoester group is hydrolyzed in the aqueous work-up. The compound of the formula III is obtained without an additional cleavage step being necessary. The compounds of the formula III are not purified, because they are obtained as a diastereomeric mixture. The crude product is obtained in nearly 100% yield and contains more than 90% of the desired product III according to HPLC-analysis. The compounds IV is obtained essentially pure (>98% according to HPLC analysis) in about 90% yield related to compound III.

The dehydration of the compound of formula III can be carried out in a manner known per se. Expediently, this reaction is carried out by treatment with an acid such as, for example, sulfuric acid, hydrochloric acid, p-toluenesulfonic acid and the like. The solvent used is expediently one of those which forms an azeotrope with the water formed, for example aromatic hydrocarbons such as benzene, toluene, xylene and the like. The dehydration is also advantageously carried out at elevated temperature, preferably at the reflux temperature of the reaction mixture.

The compound of the formula IV obtained after dehydration is, already mentioned, a known compound (for example EP A 084 377) and can be easily converted into D-(+)-biotin in a known manner, i.e., by alkaline hydrolysis, hydrogenation of the double bond and removal of the protective groups on the nitrogen atoms (for example Swiss Patent 556,867).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of German P 41 07 121.2, filed Mar. 6, 1991, are hereby incorporated by reference.

EXAMPLES

Example 1

Synthesis of methyl 5-chlorimidopentanoate hydrochloride 24.94 g (210 mmol) of 5-chlorovaleronitrile are dissolved in 210 ml of absolute diethyl ether and 8.08 g (252 mmol) of absolute methanol 19.2 g (525 mmol) of dried HCl gas are passed in at room temperature in the course of 4 h. The reaction solution is cooled and allowed to stand for 120 h.

The precipitated crystals are filtered off with suction under nitrogen, and washed with $2 \times 100$ ml of diethyl ether and 150 ml of n-hexane.

The following are prepared analogously:
Ethyl 5-chlorimidopentanoate hydrochloride
Propyl 5-chloroimidopentanoate hydrochloride

Example 2

Synthesis of trimethyl 5-chloroorthopentanoate 35.36 g (190 mmol) of methyl 5-chloroimidopentanoate hydrochloride are suspended in 470 ml of n-hexane under nitrogen. 18.3 g (570 mmol) of methanol are then added and then the suspension is vigorously stirred at room temperature for 48 h.

The reaction solution is filtered off from the precipitated ammonium chloride with suction and concentrated, and the residue is distilled in vacuo with the addition of 0.3 g of potassium carbonate.

B.p.: 58°-59° C. (1.1 torr)

The following are prepared analogously:
Triethyl 5-chloroorthopentanoate
Tripropyl 5-chloroorthopentanoate

Example 3

Synthesis of methyl cis-2-oxo-1,3-dibenzyl-4-hydroxyhexahydroxy-1H-thieno[3,4-d]imidazol-4-ylpentanoate 390 mg (15.9 mmol) of magnesium turnings are suspended in 5 ml of THF under nitrogen and heated to 78° C. 3 ml of a solution of 3.0 g (15 mmol) of trimethyl 5-chloroorthopentanoate in 10 ml of THF and 100 μl of 1,2-dibromoethane are added dropwise.

After the reaction has begun, the remainder of the solution is added dropwise in the course of 5 minutes. After refluxing for 15 minutes, the reaction is diluted with 20 ml of THF and subsequently stirred for a further 15 minutes.

The reaction solution is added dropwise to a solution of 2.59 g (7.8 mmol) of (+)-cis-1,3-dibenzylhexahydro- 1H-thieno[3,4-d]imidazole-2,4-dione in 15 ml of THF; the temperature rises to 38° C. in the course of this. The reaction is subsequently stirred for 3 h.

Customary working up and chromatography gives 3.19 g (90% of theory) of methyl cis-2-oxo-1,3-dibenzyl-4-hydroxyhexahydro-1H-thieno[3,4-d]imidazol-4-ylpentanoate.

The following are prepared analogously:
Ethyl cis-2-oxo-1,3-dibenzyl-4-hydroxyhexahydro-1H-thieno[3,4-d]imidazol-4-ylpentanoate
Propyl cis-2-oxo-1,3-dibenzyl-4-hydroxyhexahydro-1H-thieno[3,4-d]imidazol-4-ylpentanoate
Propyl cis-2-oxo-1-[(1-phenylethyl)]-3-benzyl-4-hydroxyhexahydro-1H-thieno-[3,4-d]imidazol-4-ylpentanoate Example 4

Synthesis of methyl cis-2-oxo-1,3-dibenzylhexahydro-1H-thieno[3,4-d]imidazol-4-ylidenepentanoate 15 ml of 30% sulfuric acid are added dropwise to a mixture of 3.41 g (7.5 mmol) of methyl cis-2-oxo-1,3-dibenzyl-4-hydroxyhexahydro-1H-thieno[3,4-d]imidazol-4-ylpentanoate (prepared according to Example 3) and 40 ml of THF, and the mixture is heated at 55° C. for 30 minutes.

Customary working up and column chromatography with toluene/ethyl acetate 7:3 gives 2.94 g of methyl cis-2-oxo-1,3-dibenzylhexahydro-1H-thieno[3,4-d]imidazol-4-ylidenepentanoate (90% of theory), $[\alpha]_D^{25} = +230.4$ (c=1, benzene)

The following are prepared analogously:
Ethyl cis-2-oxo-1,3-dibenzylhexahydro-1H-thieno[3,4-d]imidazol-4-ylidenepentanoate
Propyl cis-2-oxo-1,3-dibenzylhexahydro-1H-thieno[3,4-d]imidazol-4-ylidenepentanoate
Propyl cis-2-oxo-1-[(R)-(1-phenylethyl)]-3-benzyl-4-hydroxyhexahydro-1H-thieno·[3,4-d]imidazol-4-yl-pentanoate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a compound of formula III

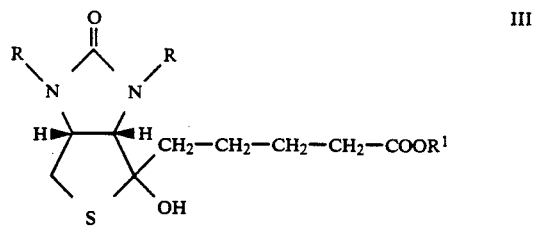

comprising reacting a thiolactone of formula I

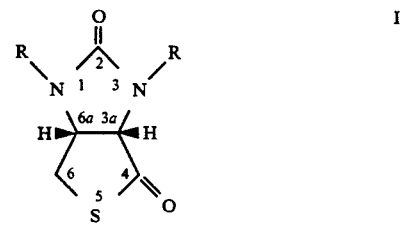

wherein R is a benzyl group which is unsubstituted or substituted by one or two alkyl groups having 1 to 5 C atoms, with an organometallic compound of formula II

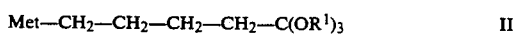

wherein Met is Li, MgCl or MgBr, and $R^1$ is alkyl having 1 to 3 C atoms.

2. A process according to claim 1, wherein the reaction is conducted in an inert organic solvent.

3. A process according to claim 2, wherein the reaction is conducted at about −78° C. to the boiling point of the solvent used.

4. A process according to claim 2, wherein the reaction is conducted at about 0° C. to about 50° C.

5. A process according to claim 2, wherein the reaction is conducted at room temperature.

6. A process according to claim 2, wherein the solvent is a lower alkyl ether or cyclic ether.

7. A process according to claim 3, wherein the solvent is selected from diethyl ether or tetrahydrofuran.

8. A process according to claim 1, wherein 1.0–1.3 moles of organometallic compound of formula II are reacted with 1.0 mole of thiolactone of formula I.

* * * * *